United States Patent [19]
Yamashita et al.

[11] Patent Number: 4,823,016
[45] Date of Patent: Apr. 18, 1989

[54] SCINTILLATION DETECTOR FOR THREE-DIMENSIONALLY MEASURING THE GAMMA-RAY ABSORPTION POSITION AND A POSITRON CT APPARATUS UTILIZING THE SCINTILLATION DETECTOR

[75] Inventors: Takaji Yamashita; Hiroshi Uchida; Keiji Shimizu; Tomohide Omura, all of Shizuoka, Japan

[73] Assignees: Hamamatsu Photonics Kabushiki Kaisha, Shizuoka; Research Development Corporation of Japan, Tokyo, both of Japan

[21] Appl. No.: 96,459

[22] Filed: Sep. 15, 1987

[30] Foreign Application Priority Data

Sep. 18, 1986 [JP] Japan ............................... 61-220313

[51] Int. Cl.[4] .......................... G01T 1/164; G01T 1/20
[52] U.S. Cl. ............................... 250/363.03; 250/366; 250/367; 250/368
[58] Field of Search ................. 250/368, 363 SA, 366, 250/367

[56] References Cited

U.S. PATENT DOCUMENTS

| | | | |
|---|---|---|---|
| 3,502,873 | 3/1970 | Woronowicz | 250/363 SA |
| 3,573,458 | 4/1971 | Anger | 250/363 SA |
| 3,767,915 | 10/1973 | Battist . | |
| 3,825,758 | 7/1974 | Miraldi | 250/366 |
| 3,955,088 | 5/1976 | Muehllehner et al. | 250/363 SA |
| 3,978,337 | 8/1976 | Nickles et al. | 250/367 |
| 4,057,727 | 11/1977 | Muehllehner et al. | 250/363 SA |
| 4,150,292 | 4/1979 | Ter-Pogossian | 250/363 SA |
| 4,187,427 | 2/1980 | Cusano | 250/366 |
| 4,234,792 | 11/1980 | DeCou et al. | 250/368 |
| 4,259,578 | 3/1981 | Thompson | 250/363 SA |
| 4,279,772 | 7/1981 | Takagi et al. | 250/483.1 |
| 4,284,890 | 8/1981 | Thompson | 250/363 SA |
| 4,288,424 | 9/1981 | Neirinckx et al. | 250/432 PD |
| 4,291,228 | 9/1981 | Thompson | 250/363 SA |
| 4,309,611 | 1/1982 | Tanaka et al. | 250/363 SA |
| 4,337,397 | 6/1982 | Vacher | 250/363 SA |
| 4,352,018 | 9/1982 | Tanaka et al. | 250/363 SA |
| 4,430,320 | 2/1984 | Shigematsu et al. | 424/1.1 |
| 4,439,414 | 3/1984 | Shiue et al. | 424/1.1 |
| 4,479,901 | 10/1984 | Barnette | 260/239 BD |
| 4,491,732 | 1/1985 | Pritzkow et al. | 250/366 |
| 4,510,394 | 4/1985 | Allemand et al. | 250/483.1 |
| 4,559,597 | 12/1985 | Mullani | 250/363 SA |
| 4,575,868 | 3/1986 | Ueda et al. | 250/363 SA |
| 4,617,386 | 10/1986 | Elmaleh et al. | 536/112 |
| 4,642,464 | 2/1987 | Mullani | 250/363 SA |
| 4,647,446 | 3/1987 | Sargent, III et al. | 424/1.1 |
| 4,647,779 | 3/1987 | Wong | 250/363 SA |

FOREIGN PATENT DOCUMENTS

| | | | |
|---|---|---|---|
| 2552887 | 4/1985 | France | 250/368 |
| 56-12567 | 2/1981 | Japan . | |
| 57-70476 | 4/1982 | Japan . | |
| 76466 | 5/1982 | Japan | 250/368 |
| 57-194373 | 11/1982 | Japan . | |
| 59-14244 | 1/1984 | Japan . | |
| 60-185730 | 9/1985 | Japan . | |
| 207084 | 10/1985 | Japan | 250/368 |

*Primary Examiner*—Carolyn E. Fields
*Attorney, Agent, or Firm*—Finnegan, Henderson, Farabow, Garrett, & Dunner

[57] ABSTRACT

A scintillation detector for three-dimensionally measuring the absorption position of the gamma-rays entering the detector and a positron computed tomography apparatus employing as a gamma-rays detector plural scintillation detectors arranged in the form of a ring are provided which can prevent the degradation of the spatial resolution in the peripheral region of the visual field and uniformly detect a positron distribution over the entire visual field with high resolution. The scintillation detector comprises a bundle of pillar-shaped scintillator elements and position detecting photodetectors coupled to the end surfaces of each scintillator element, and the apparatus comprises a plurality of scintillation detectors formed in a ring, each of which includes a bundle of scintillator elements, and plural position detecting photodetectors each of which is connected to both ends of the scintillator bundle.

17 Claims, 6 Drawing Sheets

POSITION OF GAMMA-RAY ABSORPTION

SCINTILLATION DETECTOR FOR THREE-DIMENSIONALLY MEASURING THE GAMMA-RAY ABSORPTION POSITION AND A POSITRON CT APPARATUS UTILIZING THE SCINTILLATION DETECTOR

BACKGROUND OF THE INVENTION

This invention relates to a scintillation detector for three-dimensionally measuring the position of gamma-ray absorption in the detector, and a positron computed tomography (CT) apparatus including plural scintillator detectors arranged in the form of a ring for uniformly obtaining high resolution over the region from the center to the periphery of a visual field without degradation of the spatial resolution in the peripheral region of the visual field.

In nuclear medical diagnosis, a drug labeled with a radioactive isotope (hereinafter referred to as an "RI") is ingested by or injected into a patient, and gamma-rays emitted from the RI in the patient's body are detected outside of the body, thereby providing the distribution of the RI within the body and enabling diagnosis of metabolic functions of internal organs of the body. It is important that the drug labeled with the RI accurately represents the metabolic functions of particular internal organs in the body. For example, where a particular RI is not an inherent element in a living body, a drug labeled with that RI causes metabolic activity and metabolic processes to be significantly changed in comparison with a drug which is not labeled, so that subsequent search for or investigation of the metabolic function is frequently difficult.

A living body is composed of elements including H, C, N and O. These elements also contribute to the metabolism of the living body. A drug labeled with a positron emitter such as $^{11}C$, $^{13}N$, $^{15}O$, or the like, can accurately represent the metabolic function because substances participating in the metabolism, such as C, N, O and the like, are merely replaced by their isotopes and as a result no change is made in chemical structure. Therefore, positron CT for detecting positron nuclides is useful in the field of nuclear medical diagnosis.

Figure 9A:
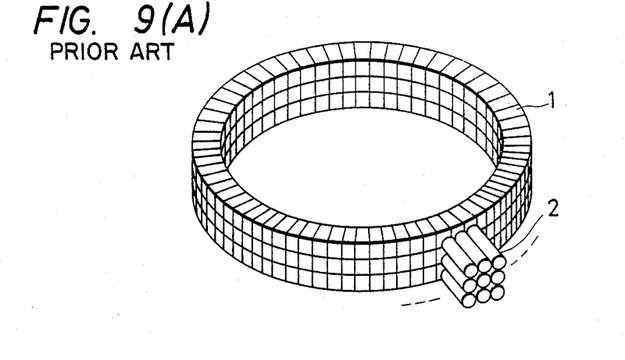
FIG. 9(A) shows a scintillation detector comprising scintillators and photodetectors connected to the scintillators in the ratio of one to one.
Figure 9B:
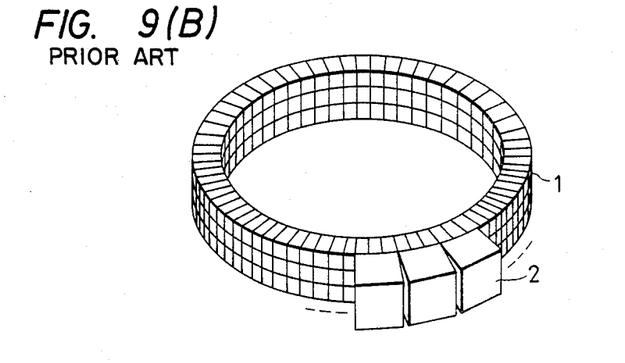
FIG. 9(B) shows a scintillation detector in which scintillators are connected to photodetectors in the ratio of N scintillators to one photodetector.
Figure 9C:
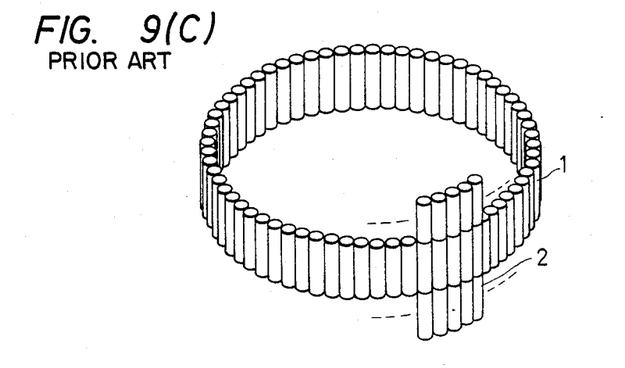
FIG. 9(C) shows a ring-shaped scintillation detector comprising cylindrical scintillators and photodetectors connected to both sides or ends of the respective cylindrical scintillators.

FIG. 9 shows a conventional gamma-ray detector employed in a conventional positron CT apparatus. FIG. 9(A) shows a gamma-ray detector comprising a number of scintillators 1 arranged in the form of a ring and photodetectors 2 connected to the scintillators at a ratio of one to one. FIG. 9(B) shows a detector in which scintillators 1 are connected to photodetectors 2 at a ratio of N scintillators to one photodetector, where N is an integer. FIG. 9(C) shows a gamma-ray detector comprising cylindrical scintillators 1 and photodetectors 2 connected to both sides or ends of the scintillators.

In a positron CT apparatus having a gamma-ray detector as described above, two of the scintillators arranged in the form of a ring simultaneously detect two gamma-rays propagating in opposite directions which are radiated when positrons emitted from the RI combine with electrons and are thereby annihilated. A distribution of RIs on a circular plane (hereinafter referred to as "as visual field") defined by the scintillators arranged in the form of a ring can then be observed.

The positron CT apparatus as described above has disadvantage in that spatial resolution is degraded in a peripheral region of the visual field of the apparatus. Moreover, this disadvantage becomes more pronounced as individual scintillators are designed to be narrower to increase their resolving power and longer to increase gamma-ray detection efficiency and sensitivity. Such a problem is caused by the structure and arrangement of the scintillators.

SUMMARY OF THE INVENTION

In order to overcome this disadvantage, the present invention provides a positron CT apparatus with a new type of scintillation detector for detecting gamma-rays and three-dimensionally measuring the position of gamma-ray absorption therein, to thereby reduce or prevent the degradation of the spatial resolution in the peripheral region of the visual field and display a positron distribution uniformly over the entire visual field with high resolution.

The scintillation detector according to the present invention comprises a scintillator bundle comprising plural scintillator elements made up into a bundle for emitting scintillation light incident to absorption of gamma-rays in the scintillator elements, each of the scintillator elements having two connecting end surfaces for outputting the scintillation light and side surfaces for leading the scintillation light to the connecting end surfaces and a position detecting photodetector coupled to the connecting end surfaces of each of the scintillator elements, for receiving the scintillation light from the connecting end surfaces and outputting the electrical signals corresponding to the scintillation light, and a positron CT apparatus according to this invention comprises a plurality of scintillation detectors arranged in the form of a ring, each of the scintillation detectors comprising a bundle of plural pillar-shaped scintillator elements and a position detecting photodetector connected to each end of the scintillator bundle.

BRIEF DESCRIPTION OF THE DRAWINGS

The accompanying drawings, which are incorporated in and constitute a part of this specification, illustrate a preferred embodiment of the invention and, together with the description, serve to explain the principles of the invention. In the drawings:

FIG. 5 illustrates a procedure for determining a gamma-ray absorption position in each coordinate of a scintillator element, in which

FIG. 9 shows a conventional positron CT apparatus, in which

DESCRIPTION OF THE PREFERRED EMBODIMENT

Figure 10:
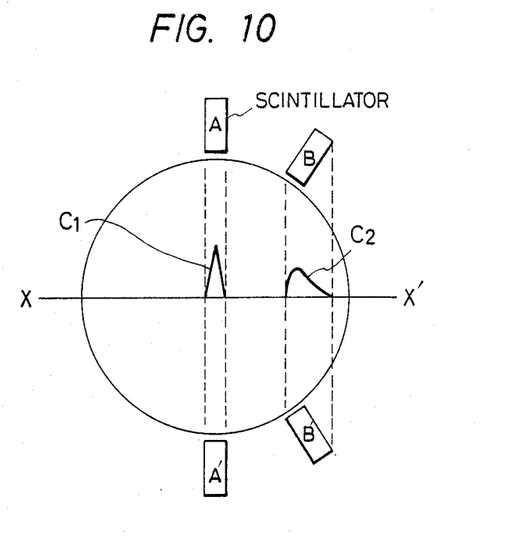
FIG. 10 shows a coincidence sensitivity for each pair of detectors on a line X—X'; distribution for and FIG. 11 shows the relationship of resolving power with the distance from the center of the ring-shaped scintillation detector.

FIG. 10 shows a coincidence sensitivity distribution of each pair of detectors on a line X—X' which passes through the center of the detector ring. In FIG. 10, a line connecting a pair of detectors (A and A') passes through the center of the visual field and a line connecting another pair of detectors (B and B') passes through the peripheral region of the visual field. $C_1$ and $C_2$ represent coincidence response functions in the center and the peripheral regions of the visual field respectively.

As shown in FIG. 10, when a point-type gamma-ray source is shifted along the line X—X' and detector pairs (A—A' and B—B') are used to coincidentally count the gamma-rays, response functions, that is, coincidence sensitivity distributions, of respective detector pairs which are designated by $C_1$ for detector pair A—A' and $C_2$ for detector pair B—B', are obtained.

The width of the response function approximately represents a positional or spatial resolution in the radial direction. The response function $C_1$ in the center of the visual field which is detected by detector pair A—A' has a symmetrical triangular distribution and its spatial resolution approximately corresponds to a half width of a scintillator.

The response function $C_1$ is not dependent on the position (in the depth-direction of a scintillator) where gamma-rays are absorbed in the scintillator. On the other hand, the response function $C_2$ in the peripheral region of the visual field has a surprisingly broad distribution, and consequently the spatial resolution is degraded.

Figure 11:
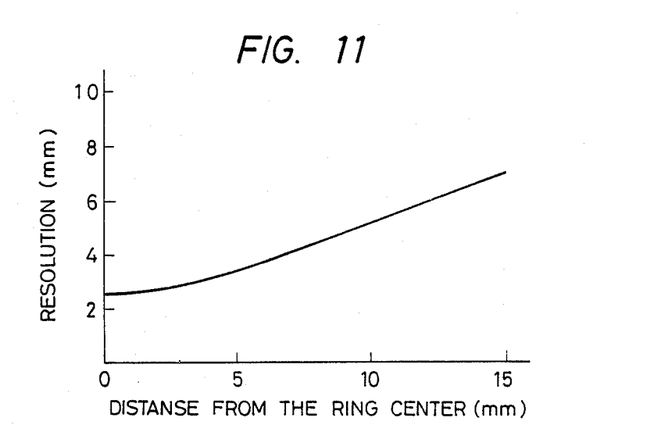

FIG. 11 shows the relationship between positional or spatial resolution in the radial direction and the distance from the center of the ring-shaped detector where the diameter of the ring, and the width and the length of each scintillator are 540 mm, 5 mm and 30 mm, respectively. As is apparent in FIG. 11, the spatial resolution is degraded more significantly as the detecting position approaches the peripheral region of the visual field.

A positron CT apparatus according to the present invention includes a plurality of scintillation detectors arranged in the form of a ring, each of which comprises a scintillator bundle formed by binding pillar-shaped scintillator elements into a bundle. A position detecting photodetector is connected to each end of the scintillator. Accordingly, three-dimensional position information of the gamma-ray absorption in the scintillator can be obtained, and a positron emitter distribution with high resolution in the peripheral region of the visual field as well as in the center region thereof can be obtained. Additionally, one can simultaneously obtain a number of sliced or cross-sectional images.

Figure 1:
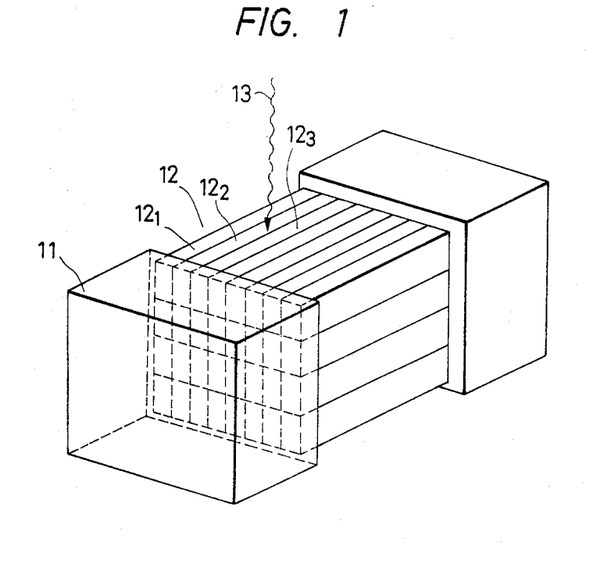
FIG. 1 shows an embodiment of a scintillation detector according to the present invention.

FIG. 1 shows an embodiment of a scintillation detector according to the present invention. In FIG. 1, reference numeral 11 represents a position detecting photodetector, 12 represents a scintillator bundle, $12_1$, $12_2$ and $12_3$ represent scintillator elements, and 13 represents incident gamma-rays.

In FIG. 1, each of the scintillator elements $12_1$, $12_3$ and $12_3$ is in the form of a pillar and comprises, for example, bismuth germanium oxide(BGO). Each of the pillar-shaped scintillator elements has two end surfaces, each of which can be mated with or connected to a receiving surface of photodetector. Each scintillator also has at least one side wall or surface typically substantially perpendicular to the end surface, through which gamma-rays may enter, as shown in FIG. 1. Scintillator bundle 12 is formed by binding the scintillator elements into a bundle. The end surfaces of each of the scintillator elements are mirror polished. It is preferable to totally reflect scintillation light at the inner surface of the side walls of each scintillation element and to reflect the light to one or both end surfaces thereof. This may be accomplished by coating any surfaces other than the mirror polished end surfaces with a reflecting material such as barium sulphate($BaSO_4$) or the like, or by providing spacing or an air gap between respective neighboring scintillator elements, or by combining both the coating and the inter-element spacing. Both ends of the scintillator bundle 12 thus formed are connected to a two-dimensional position detecting type of photomultiplier having, for example, a crossed multiwire-anode. The coupling of the scintillator bundle to the two-dimensional photodetector may be formed directly or through a light guide.

Figure 2:
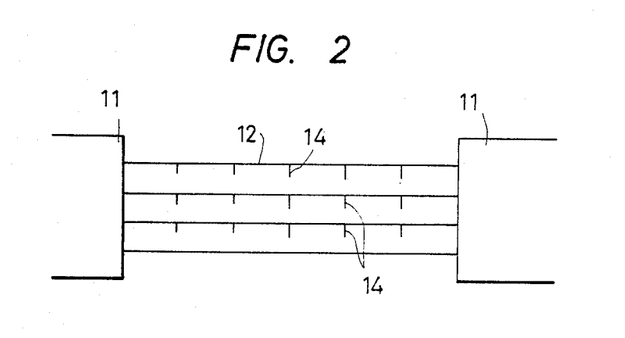
FIG. 2 shows a scintillation detector in which plural incisions are made in the direction parallel to a connecting surface of each scintillator element which contacts a photodetector.

To improve the accuracy in position detection, roughly-ground portions may be provided on any surface (side surface) of each scintillator element other than connecting surfaces (end surfaces). Preferably, plural incisions 14 are formed on the side surfaces of each scintillator element parallel to the connecting end surfaces. FIG. 2 shows a detector having plural incisions 14 formed on each scintillator element in the direction parallel to the connecting surface of the scintillator element.

Figure 3:
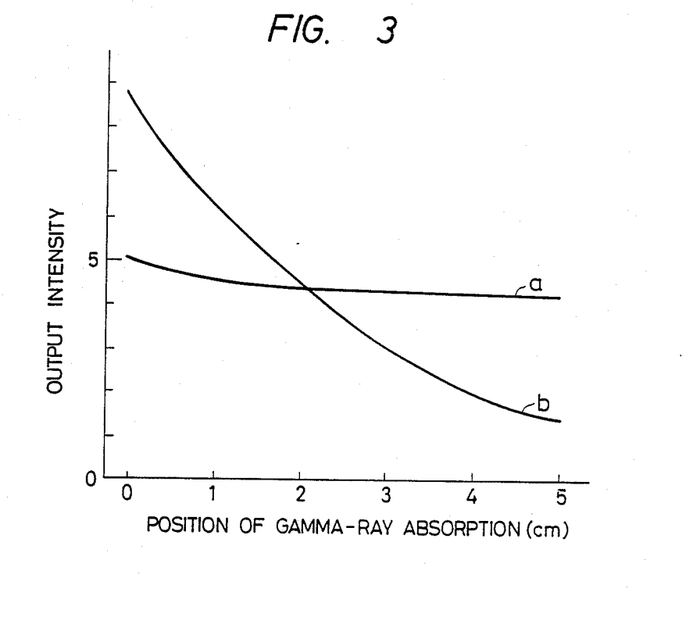
FIG. 3 is a graph showing an effect obtained by providing a roughly-ground portion on each scintillator element.

FIG. 3 is a graphical representation which illustrates an effect obtained by forming a roughly-ground portion on each scintillator element. In FIG. 3, the abscissa of the graph represents a gamma-ray absorbing position and the ordinate represents an output intensity from an end of a scintillator element ($3 \times 5 \times 50$ mm).

The curve (a) represents an output intensity of a scintillator element having mirror polished side surfaces coated with a reflecting material. Curve (b) represents a scintillator element having roughly ground side surfaces coated with the reflecting material.

Figure 4:
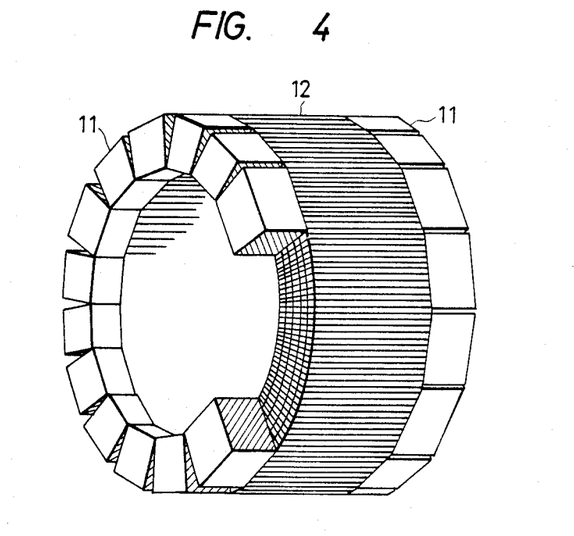
FIG. 4 shows an embodiment of a positron CT apparatus using the scintillation detector according to the present invention.

As is apparent in FIG. 3, the inclination of the output intensity distribution of a scintillator element can be made steeper by roughly grinding the side surfaces of the scintillator element, thus the accuracy of detecting position can be improved. The scintillation detector thus formed is arranged in the form of a ring, as shown in FIG. 4, and employed as a gamma-ray detector in a positron CT apparatus.

Figure 5A:
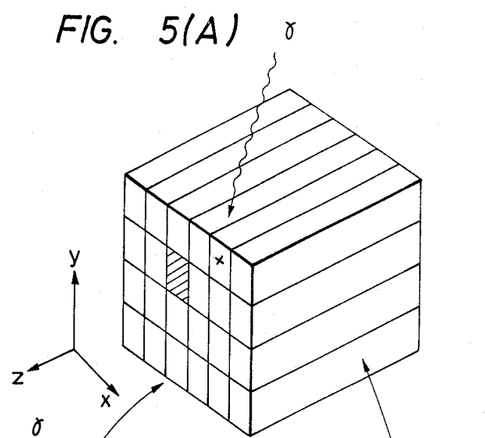
FIG. 5(A) is a perspective view of scintillator bundle.
Figure 5B:
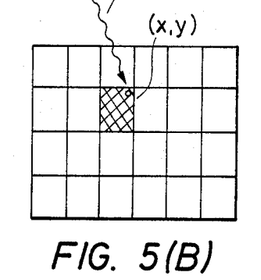
FIG. 5(B) is a plane view of the bundle.
Figure 5C:
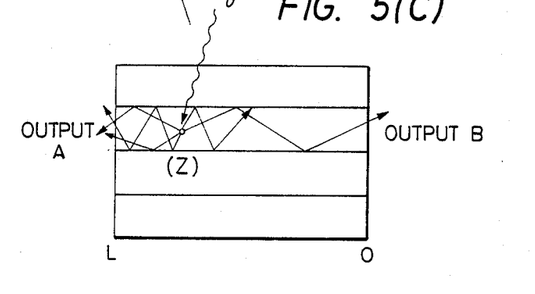
FIG. 5(C) is a sectional view of the bundle.
Figure 6:
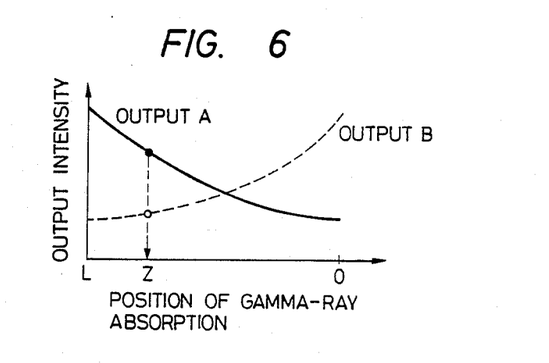
FIG. 6 is an explanatory diagram for determining a gamma ray absorption position in the Z-coordinate.

FIGS. 5 and 6 are explanatory diagrams for explaining the principle of the detector according to this invention. Scintillation light is emitted from both ends of a scintillator element when gamma-rays are absorbed in the scintillator element. The scintillation light thus emitted is detected by position detecting photodetectors connected to each scintillator bundle. On the basis of the output of the photodetectors, an incident position of the gamma-ray is calculated to determine the coordinate position (X, Y).

FIG. 6 shows the relationship between the output intensity of an output A,B with the position of the gamma-ray absorption (along the z-axis). The position of gamma-ray absorption along the Z-coordinate is obtained by comparing the output intensity of the outputs A with that of output B, as shown in FIG. 6.

As the position of gamma-ray absorption in the y-direction of a scintillator can be determined as described above, high spatial resolution can be obtained in a peripheral region of a visual field as well as in the center region of a visual field. Further, detecting units can be densely arranged to obtain high sensitivity, and spatial information in the z-direction can be obtained, thus, simultaneously obtaining multi-sliced tomographic images.

Figure 7:
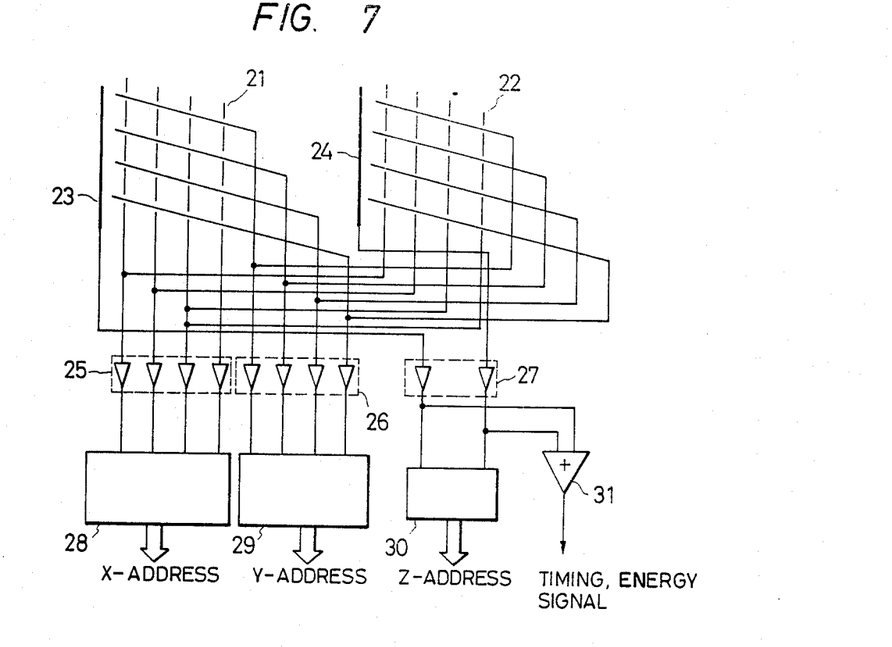
FIG. 7 shows an embodiment of a signal read-out circuit in the detector according to the present invention.

FIG. 7 shows an embodiment of a signal read-out circuit in a position detecting photodetector according to the present invention. In FIG. 7, reference numerals 21 and 22 represent wire anodes of two position detecting photomultipliers connected to each end of a scintillator bundle; 23 and 24 are respective dynodes of the photomultipliers; 25, 26 and 27 are buffer amplifiers; 28, 29 and 30 are x-, y- and z-position calculating circuits, respectively; and 31 is an adder.

As shown in FIG. 7, respective outputs detected by the wire anodes are applied through the buffer amplifiers 25 and 26 to the x- and y-position calculating circuits 28 and 29 and subjected to respective positioning calculations therein. X-address and y-address signals are the outputted from the x-position and y-position calculating circuits, respectively. Furthermore, signals from the dynodes 23 and 24 are independently applied to the buffer amplifiers 27 and the outputs thus amplified are applied to z-position calculating circuit 30 and adder 31 so that a z-address signal is outputted from z-position calculating circuit 30, and an energy signal and a timing signal are outputted from adder 31.

Figure 8:
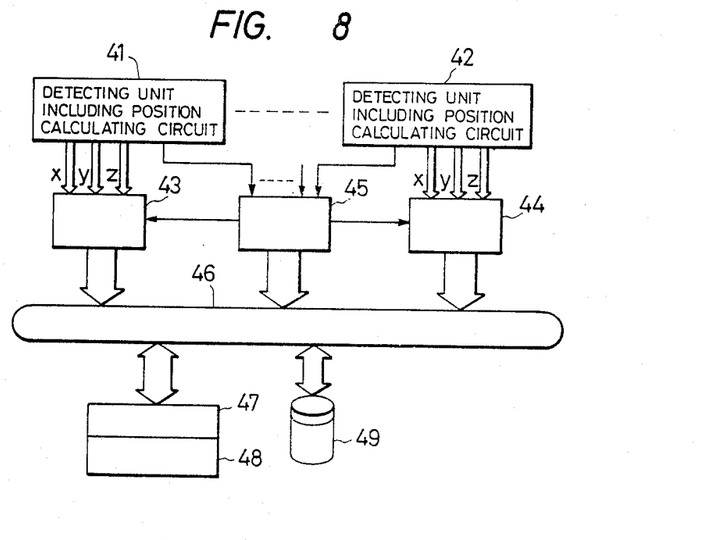
FIG. 8 shows a circuit arrangement of a positron CT apparatus according to the present invention.

FIG. 8 shows a circuit arrangement of a positron CT apparatus employing the scintillation detector according to the present invention. Reference numerals 41 and 42 represent detecting units for detecting a pair of gamma-rays propagating in opposite directions from each other; 43 and 44 are data selectors; 45 is a coincidence counting circuit; 46 is data bus; 47 is a main memory unit; 48 is a data processing unit; and 49 is an auxiliary memory unit.

When the two detecting units 41 and 42 of the plurality of detecting units arranged in the form of a ring detect a pair of gamma-rays generated by the annihilation of positrons, the outputs from the two detecting units are analyzed by the coincidence counting circuit 45 (using a timing signal) to determine whether or not the outputs were received simultaneously with each other within a given period of time. If the outputs are found to be simultaneously counted, respective address signals (x, y, z) are selected by data selectors 43 and 44 and provided to data bus 46. At this time, unit addresses pointing to the scintillation detectors which detect the gamma rays also are provided to data bus 46. The data included in the address signals and the unit addresses are stored in main memory unit 47 or auxiliary memory unit 49, and are then subjected to ordering and pre-processing operations in data processing unit 48 to reconstruct a corresponding image.

As described above, the scintillation detector of the present invention which comprises a bundle of pillar-shaped scintillator elements generates three-dimensional information on the gamma-ray absorption position. By providing a positron CT apparatus with plural scintillation detectors as described above and utilizing the three-dimensional information obtained by each scintillation detector, spatial resolution in the peripheral region of the visual field can be improved and high sensitivity can be obtained uniformly, so that a position CT apparatus having simple construction and high spatial resolution is obtained.

Furthermore, a positron CT apparatus employing the scintillation detector according to this invention has the advantages that multi sliced tomographic images can be simultaneously obtained and high sensitivity can be obtained by the dense arrangement of the detectors.

Additional advantages and modifications will readily occur to those skilled in the art. Therefore, the invention in its broader aspects is not limited to the specific details, representative devices, and illustrative examples shown and described. Accordingly, departures may be made from such details without departing from the spirit or scope of the general inventive concept as defined by the appended claims and their equivalents.

What is claimed is:

1. A scintillation detector for detecting gamma-rays, said detector comprising:

a scintillator bundle comprising a plurality of scintillator elements for emitting scintillation light incident to absorption of gamma-rays in said scintillator elements, each of said scintillator elements having two connecting end surfaces for outputting said scintillation light and said surfaces for leading said scintillation light to said connecting end surfaces; and a position detecting photodetector coupled to said connecting end surfaces of each of said scintillator elements, said position detecting photodetector receiving said scintillation light from said connecting end surfaces and outputting electrical signals corresponding to an output intensity of said scintillation light to calculate an incident direction of said gamma-rays, wherein said position detecting photodetector further comprises position calculating means for receiving said electrical signals and three-dimensionally calculating the position of gamma-ray absorption in said scintillator bundle.

2. A scintillation detector as claimed in claim 1, wherein each of said scintillator elements is pillar-shaped.

3. A scintillation detector as claimed in claim 1, wherein said connecting end surfaces of each of said scintillation elements are mirror polished.

4. A scintillation detector as claimed in claim 1, wherein at least a portion of said side surfaces are coated with a reflecting material.

5. A scintillation detector as claimed in claim 4, wherein spacing is provided between adjacent ones of said scintillator elements.

6. A scintillation detector as claimed in claim 1, wherein spacing is provided between adjacent ones of said scintillator elements.

7. A scintillation detector as claimed in claim 1, wherein said side surfaces of said scintillator elements are roughly ground.

8. A scintillation detector as claimed in claim 1, wherein plural incisions are formed on said side surfaces of each of said scintillator elements in the direction parallel to said connecting end surfaces of said scintillator elements.

9. A scintillation detector as claimed in claim 1, wherein said scintillator elements are coupled to said position detecting photodetector through a light guide, said light guide leading said scintillation light from each of said connecting surfaces to said position detecting photodetector.

10. A scintillation detector as claimed in claim 1, wherein said position detecting photodetector comprises a photomultiplier including a crossed multiwire-anode for converting said scintillation light into said electrical signals.

11. A positron computed tomography apparatus for three-dimensionally measuring the position of a gamma-ray emitting source comprising:
a plurality of scintillation detectors arranged in the form of a ring, each of said scintillation detectors comprising a bundle of plural pillar-shaped scintillator elements for emitting scintillation light incident to absorption of gamma rays therein, each scintillator element having two connecting end surfaces for emitting said scintillation light and side surfaces for leading said scintillation light to said connecting end surfaces;
a plurality of position detecting photodetectors, each photodetector coupled to said connecting end surfaces of each of said scintillator elements, for receiving said scintillation light from said connecting end surfaces and three-dimensionally measuring the position of gamma-ray absorption in said bundle; and
position determinang means for determining a pair of scintillation detectors coincidentably detecting a pair of gamma rays propagating in opposite directions to each other and three-dimensionally calculating the position of said gamma-ray emitting source on the basis of the three-dimensional information of said pair of scintillation detectors.

12. A positron computed tomography apparatus as claimed in claim 11, wherein at least a portion of the side surfaces of said scintillator elements is coated with a reflecting material.

13. A positron computed tomography apparatus as claimed in claim 11, wherein spacing is provided between adjacent ones of said scintillator elements.

14. A positron computed tomography apparatus as claimed in claim 12, wherein spacing is provided between adjacent ones of said scintillator elements.

15. A positron computed tomography apparatus as claimed in claim 11, wherein the side surfaces of said scintillator elements are roughly ground.

16. A positron computed tomography apparatus as claimed in claim 11, wherein a plurality of incisions are formed on the side surfaces of said scintillator elements in a direction parallel to the end surfaces of said scintillator elements.

17. A positron computed tomography apparatus as claimed in claim 11, wherein said scintillator elements are coupled to said photodetector through a light guide.

* * * * *